(12) United States Patent
Tchakalova et al.

(10) Patent No.: US 9,976,108 B2
(45) Date of Patent: *May 22, 2018

(54) ETHANOL-FREE MICROEMULSION PERFUMING COMPOSITIONS

(71) Applicant: FIRMENICH SA, Geneva (CH)

(72) Inventors: Vera Tchakalova, Geneva (CH); Valeria Hafner, Geneva (CH)

(73) Assignee: Firmenich SA, Geneva (CH)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/613,999

(22) Filed: Jun. 5, 2017

(65) Prior Publication Data

US 2017/0267943 A1    Sep. 21, 2017

Related U.S. Application Data

(63) Continuation of application No. 14/652,124, filed as application No. PCT/EP2013/076435 on Dec. 12, 2013, now Pat. No. 9,701,924.

(30) Foreign Application Priority Data

Dec. 13, 2012  (EP) .................................. 12196964

(51) Int. Cl.

| | | |
|---|---|---|
| *A61K 8/37* | (2006.01) | |
| *C11B 9/00* | (2006.01) | |
| *A61K 8/34* | (2006.01) | |
| *A61K 8/60* | (2006.01) | |
| *A61Q 19/00* | (2006.01) | |
| *A61K 8/06* | (2006.01) | |
| *A61K 8/92* | (2006.01) | |
| *A61Q 13/00* | (2006.01) | |

(52) U.S. Cl.
CPC ............ *C11B 9/0003* (2013.01); *A61K 8/068* (2013.01); *A61K 8/345* (2013.01); *A61K 8/37* (2013.01); *A61K 8/60* (2013.01); *A61K 8/604* (2013.01); *A61K 8/922* (2013.01); *A61Q 13/00* (2013.01); *A61Q 19/007* (2013.01); *A61K 2800/30* (2013.01)

(58) Field of Classification Search
CPC ...................................................... A61K 8/345
See application file for complete search history.

(56) References Cited

U.S. PATENT DOCUMENTS

| | | |
|---|---|---|
| 4,488,989 A | 12/1984 | Lamberti |
| 5,468,725 A | 11/1995 | Guenin et al. |
| 6,359,168 B1 | 3/2002 | Frerot et al. |
| 2006/0165739 A1 | 7/2006 | Komesvarakul et al. |
| 2007/0161526 A1 | 7/2007 | Vlad et al. |
| 2011/0081393 A1 | 4/2011 | Komatsuki et al. |
| 2011/0177995 A1 | 7/2011 | Fraser et al. |

FOREIGN PATENT DOCUMENTS

| | | |
|---|---|---|
| EP | 1 034 161 B2 | 9/2000 |
| EP | 1 040 765 A1 | 10/2000 |
| WO | 95/12379 A1 | 5/1995 |
| WO | 99/28288 A1 | 6/1999 |

OTHER PUBLICATIONS

International Search Report and Written Opinion, Appl. No. PCT/EP2013/076435, dated May 9, 2014.
U.S. Appl. No. 14/652,124, Non-Final Rejection, dated Apr. 25, 2016.
U.S. Appl. No. 14/652,124, Final Rejection, dated Nov. 17, 2016.
U.S. Appl. No. 14/652,124, Notice of Allowance, dated Mar. 7, 2017.

*Primary Examiner* — Benjamin Packard
(74) *Attorney, Agent, or Firm* — Winston & Strawn LLP

(57) ABSTRACT

The present invention provides a perfuming composition that is free of ethanol and that is in the form of a transparent, clear microemulsion that contains a fragrance at a concentration of 0.5 to 50% by weight; a solvent at a concentration of 1 to 36% by weight; a non-ionic surfactant at a concentration of 1 to 35% by weight; an ionic surfactant at a concentration of 0 to 12% by weight, a cooling hydrotrope at a concentration of 0.01 to 12% by weight and water. Said microemulsions benefit from the presence of a cooling hydrotrope which allows lowering the amount of surfactant needed and provides a cooling effect.

19 Claims, No Drawings

ETHANOL-FREE MICROEMULSION PERFUMING COMPOSITIONS

CROSS-REFERENCE TO RELATED APPLICATIONS

This application is a continuation of U.S. patent application Ser. No. 14/652,124 filed Jun. 14, 2015, which is a 371 filing of International application no. PCT/EP2013/076435 filed Dec. 12, 2013, which claims priority to European patent application no. 12196964.6 filed Dec. 13, 2012, the entire contents of each of which are incorporated herein by reference thereto.

TECHNICAL FIELD

The invention relates to cosmetic alcohol-free and in particular ethanol-free microemulsions with improved solubilisation of oil, comprising a cooling agent which also acts as a hydrotrope. These formulations advantageously contain reduced quantities of surfactant thanks to the unexpected hydrotrope properties of the cooling agent but also deliver a cooling effect provided by said cooling agent.

BACKGROUND ART

Generally speaking, water-based microemulsions containing perfumes or flavors, or yet other hydrophobic active materials, have already been reported in the prior art. Frequently, these prior known microemulsions, in order to provide proper dispersion of the oil in the water-based medium, contain large amounts of short chain alcohols, namely ethanol, or other ethanol materials.

However, ethanol is considered as a Volatile Organic Compound ("VOC"). By "VOC" what is meant is a compound defined by the Environmental Protection Agency, or by EC Directive 1999/13/EC (Solvent Emissions Directive) as organic compound having a vapour pressure of 0.01 kPa or more at 293.15 K (20° C.), or having a corresponding volatility under particular conditions of use.

In the fragrance field, there is a need and there would be advantages in finding alternatives to these conventional microemulsions, in particular ethanol-free alternatives, while retaining all of the microemulsion's positive aspects, such as sensorial performance, sprayability, diffusity, and skin feel, which are associated with the presence of such short chain alcohols and in particular with ethanol.

The replacement of ethanol is very challenging for the perfumer due to the beneficial characteristics of this ingredient in perfume formulations. Indeed ethanol is an ideal solvent for perfumery ingredients, e.g. it evaporates rapidly and does therefore not disturb the odor of the perfume after its short time of evaporation. Another key characteristic of ethanol is its wetting power, which allows good spreadability of the perfume on the skin and in turn controls the diffusion of the perfume at a later step. The fast evaporation of ethanol also adds a somewhat refreshing aspect to the formulation; a characteristic that is highly appreciated by the customer.

Low VOC microemulsions have been reported in the prior art. Generally in formulating such microemulsions, it is necessary to increase the total amount of surfactants so as to obviate the absence of VOCs, otherwise the final emulsions display a lack of clarity and/or stability problems, and this is not acceptable for the perfume and flavor applications. The increase in the amount of surfactants in the final microemulsion typically results in products containing surfactant systems that are often in large excess with respect to the solubilized oil, namely the perfume or flavor. Obviously, a large excess of surfactant is also a disadvantage for such final products, in particular for perfumes or other products intended for application to the skin, hair or surfaces such as textiles, wherein high surfactant content can lead to foamy, sticky, irritating or allergenic products that are unacceptable to consumers.

US 2006/0165739 discloses the preparation of alcohol-free microemulsions and methods for their use in cosmetic compositions. These microemulsions include a surfactant, a lipophilic and hydrophilic linker, a co-oil and can include a hydrotrope. These hydrotropes are present at a concentration between 0.001 and 30% and are used as agents that increase the solubility of other organic substances in water. Specifically, ammonium xylene sulfonate, sodium xylene sulfonate, sodium mono or dimethyl naphthalene sulfonate, and alkyl glucosides are mentioned as suitable hydrotropes.

U.S. Pat. No. 4,488,989 discloses aqueous compositions containing urea as a hydrotrope, and in particular liquid detergents of improved storage stability. Urea is used in combination with a hydrolysable ester as the storage stability promoting component. Ethanol is present in such formulations up to a concentration of 10%.

US 2011/0177995 discloses an EtOH-free microemulsion, which needs a 1/1 to 5/1 mixture of non-ionic/ionic surfactant. The ionic surfactant is mandatory and in amount quite important and this can be an issue as ionic surfactants do have in general negative effects on the over performance of a perfuming composition once applied on the skin.

U.S. Pat. No. 5,468,725 describes an EtOH-free microemulsion, which is defined in a way that makes it difficult to retrieve the ratio of surfactant and perfume and exemplifies a fragrance oil that does not specify how much solvent and oil are in the fragrance—with a 100/2 mixture of non-ionic/ionic surfactant. There is no mention of use of a hydrodrope to decrease the amount of surfactant, and the amount of surfactant used is still considered to be quite high compared to the perfume amount (w/w perfume/surfactant ratio of about 0.38).

Therefore, there is a need for an alcohol-free perfume formulation that is sprayable, stable, transparent, that has moreover a light skin feel as close as possible to the one of ethanol containing compositions, having the lowest possible amount of surfactant and that can contain useful amounts of fragrance oil (which depend on the intended use). Last but not the least, said alcohol-free perfume formulation should advantageously also have a superior profile for fragrance or olfactive delivery. These are requirements needed to satisfy the current need in the perfuming field.

DETAILED DESCRIPTION OF THE INVENTION

Unless stated otherwise, % are meant to designate percent by weight of the composition. Percentages of surfactants correspond to a percentage in active matter.

The present invention resolves the deficiencies of the prior art by providing a perfuming composition in the form of a transparent and EtOH-free microemulsion comprising:
- 0.5% to 50% of a fragrance oil;
- 1.0% to 36% of a solvent;
- a surfactant system comprising:
  - a) at least a non-ionic surfactant present in an amount of 1.0% to 35%; and
  - b) at least a ionic surfactant present in an amount of 0% to 12%;

0.01% to 12% of at least a cooling hydrotrope; and
water;
wherein the perfuming composition remains stable during freeze-thaw cycles from −25° C. to 50° C., and wherein all concentrations are based on the weight of the composition.

The amount of water in the perfuming compositions of the invention can vary such that the compositions can be in the form of a more "concentrated" product or in a more "diluted" version. Typically, in a more concentrated version, the amount of water will be up to 20%.

According to a particular embodiment of the invention, consisting of a "diluted" version of the product, the composition of the invention comprises:
0.5% to 15% of a fragrance oil;
1.0% to 25% of a solvent;
a surfactant system comprising:
  a) 1.0% to 15% of at least a non-ionic surfactant; and
  b) 0% to 5% of at least a ionic surfactant;
0.01% to 4% of at least a cooling hydrotrope; and
water;
wherein all concentrations are based on the weight of the composition. Typically in such diluted product, water will be present in amount varying between 65% and 90% by weight.

A hydrotrope in the context of the invention, also sometimes referred to as "solubilizing aid", is meant to designate a compound that is not a surfactant, but which has solubilizing properties, i.e. which allows, when used in a microemulsion, reducing the amount of surfactant used to solubilize a certain quantity of oil, while not being able to replace totally the surfactant. From a different angle, a hydrotrope allows, for a defined concentration of surfactant, increasing the concentration of oil that can be solubilized. According to a particular embodiment, the hydrotrope of the present invention is free from metal salt of organic acids.

When referring to "cooling" properties of a compound like a cooling agent or a cooling hydrotrope in the context of the present invention, it is meant a compound that evokes or prolongs a sensation of cold by modulation of the transient receptor potential (TRP) ion channels present in cold-sensitive nerve fibers of the skin or of the tongue. What is therefore not considered as cooling in the sense of the present invention is the effect provided on the skin by the evaporation of a solvent or water with a corresponding decrease in the temperature.

The compositions of the invention advantageously allow minimizing the amount of surfactant by using a compound that acts as a hydrotrope, but beyond that first advantage, the compositions present an additional benefit due to the fact that the same compound which acts as a hydrotrope is a cooling agent. The compositions of the invention are therefore particularly advantageous as they meet the criteria of being EtOH-free, transparent, non-irritating to the skin while providing a very pleasant non-sticky and proper cooling feeling on the skin.

For the sake of clarity, the % amounts are the total amount, in particular when it is mentioned "at least one" said amount is the total amount obtained by adding all the amount of each constituent of the said type. It is also understood that water is present in the appropriate amount to reach the 100%, i.e. is added up to completion to 100% w/w.

For the sake of clarity, by "transparent, clear" it is meant a microemulsion presenting a clarity preferably comprised between 0 and 90 NTU, when measured between 400 and 600 nm in a 2.5 cm cell at 25° C. By "clarity" what is meant is the measure of the light scattered, at an angle of 90°, by these microemulsions. According to a preferred embodiment of the invention, the microemulsion has clarity comprised between 0 and 50 NTU when measured under the preceding conditions.

For the sake of clarity, by "microemulsion" it is meant a dispersion that forms spontaneously and has a droplet size comprised between 10 and 150 nm, at a temperature comprised between 0° C. and 50° C. According to a particular embodiment of the invention, the present microemulsion has a droplet size comprised between 10 and 60 nm, or even between 10 and 40 nm, at a temperature comprised between 0° C. and 50° C.

For the sake of clarity, by "stable during freeze-thaw cycles" it is meant that said microemulsions also display very good stability, e.g. phase separation is not observed within a reasonable frame of time when tested with at least 5 and up to 10 freeze freeze-thaw cycles from −20° C. to RT to 50° C. (24 hours per each condition). According to a particular embodiment of the invention the invention microemulsion can also display good stability when stored 3 months at 3° C. and 45° C.

For the sake of clarity, by "fragrance oil" it is meant the usual meaning in the art, i.e. a lipophilic organic liquid that is essentially insoluble in water and being composed of one or more perfuming ingredients.

In particular, there can be used any perfuming ingredient or, as happens more often, any mixture of perfuming ingredients currently used in perfumery, e.g. of compounds capable of imparting an hedonic olfactive effect to the composition to which they are added. The perfuming ingredients can be of natural or synthetic origin. A detailed description of the ingredients would not be warranted here and, in any case, it cannot be exhaustive. Generally speaking, it can be mentioned that these ingredients belong to chemical classes as varied as alcohols, aldehydes, ketones, esters, ethers, acetates, nitriles, terpenes, hydrocarbons, nitrogenous or *sulphurous* heterocyclic compounds and essential oils of natural or synthetic origin. The nature of these ingredients can be found in specialized books of perfumery and flavor ingredients, e.g. in S. Arctander (Perfume and Flavor Chemicals, Montclair N.J., USA 1969), or similar textbooks of reference, and a more detailed description thereof is not warranted here. The selection of such ingredients is carried out by the perfumer without particular difficulty, on the basis of her/his general knowledge and as a function of the nature of the product to be modified and of the desired sensory effect, i.e. the perfuming or taste effect that is to be imparted to the consumer product to be perfumed or flavored.

Advantageously and contrary to what was known heretofore in the field of microemulsions, the system of the present invention works and provides a product with required properties over a very wide range of log P. According to a particular embodiment of the invention, said fragrance oil has a log Pmix comprised between about 1 and about 7, most preferably between 1 and 4.

For the sake of clarity, by "log Pmix" it is intended the calculated log P of the mixture of perfume ingredients, which is obtained by the formula:

$$logPmix = \sum_{i=1}^{n} x_i logP_i$$

wherein $x_i$ is the molar fraction and $log P_i$ is the calculated log P of the $i_{th}$ ingredient in the mixture of n perfumery ingredients.

Said "calculated log P" is the calculated log P for each single perfuming ingredient which can be obtained according to the program EPI suite (4.0); EPA (US Environmental Protection Agency) and Syracuse Research Corporation (SRC), 2000.

According to any one of the invention's embodiments, the fragrance oil is present in an amount of about 0.5 to 50% by weight, preferably between 0.5 and 35% and more preferably between 2.5 and 15% by weight of the formulation.

The invention's microemulsion also contains a suitable solvent, in an amount of 1 to 36% by weight, and preferably 1 to 25% by weight, or even 1 to 10% by weight. Generally said solvent is present because some perfuming ingredients are available in a more or less concentrated solution in such solvent, and for example the most commonly used solvent are a dipropyleneglycol, diethyl phthalate, isopropyl myristate, benzyl benzoate, 2-(2-ethoxyethoxy)-1-ethanol, ethyl citrate and 1,2-alkanediols with 5-10 carbons. Alternatively, said solvent can be just added to the oil for any purpose. As examples of suitable solvents, one may cite polar or non-polar low molecular weight solvents such as isoparaffins, paraffins, hydrocarbons, silicon oils, perfluorinated aliphatic ethers, glycol ethers, glycol ether esters, esters, or ketones. Non-restrictive examples of such solvents includes dimethicone or cyclomethicone, which are commercialized by Chemsil Silicon INC. under the trade names COSMETIC FLUID® 1288, and respectively COSMETIC FLUID® 1387, jojoba oil, perfluoroisobutyl methyl ether, diethyl phthalate, propylene glycols, triacetin and isopropyl myristate.

According to any one of the invention's embodiments, the solvent is a glycol such as propylene glycol. For a better skin feel in cosmetics butylene glycol or di-propylene glycol are preferred. Following a "natural" ingredient formulation, a natural 1,3-propanediol, i.e., a propylene glycol, should be used as it provides very good performance. The most preferred solvents are 1,2 or 1,3 propylene glycol, 1,2-alkanediols with 5-10 carbons, dipropylene glycol, 1,2 or 1,3-butylene glycol.

According to a particular embodiment of the invention, it is useful to have a fragrance oil/solubilizing system w/w ratio comprised between about 0.3 to 1.5.

The invention's microemulsion also contains a surfactant system containing one or two different types of raw materials.

According to any one of the invention's embodiments, it is useful to have a solvent/surfactant system w/w ratio comprised between about 0.2 and 4, preferably between about 0.25 and 2.0.

A first type of raw material of the solubilizing system, and mandatory, is a non-ionic surfactant. Many different types of non-ionic surfactants can be used. According to any one of the invention's embodiments, in particular and as non-limiting examples one may cite those belonging to the classes of:

- sugar ester compound such as sucrose esters with $C_8$-$C_{20}$ fatty acid (such as sucrose esters with oleic, palmitic or stearic acid, such as a sucrose monopalmitate, e.g. Habo Monoester P90® commercialized by Compass Foods Corporation),
- $C_{8-22}$-alkyl polyglucosides (such as those sold under the name Plantacare® by BASF); e.g. fatty alcohol glucosides such as $C_8$-$C_{16}$ alkyl glucoside, e.g. decylglucoside (known also as Plantacare® 2000UP), $C_{12}$-$C_{16}$ alkyl glucoside, e.g. laurylglucoside (known also as Plantacare® 1200UP), $C_8$-$C_{16}$ alkyl glucoside, e.g. cocoglucoside (known also as Plantacare® 818UP), $C_8$-$C_{10}$ alkyl glucoside, e.g. caprylyl/caprylglucoside (known also as Plantacare® 810UP); or combination thereof with a fatty acid e.g. cocoglucoside and glyceryl oleate (known also as Lamesoft® PO 65 by BASF),
- ethoxylated aliphatic $C_6$-$C_{20}$ alcohols containing 2 to 30 EO and/or PO units (EO being ethyleneoxide and PO being propylene oxide) and in particular a $C_{11-15}$ alcohol ether with 9 EO units (such as Tomadol® 1-9 or Tomadol® 25-9), a butyl alcohol ether with 24 to 27 EO and/or PO oxide units (such as PPG-24 Buteth-26 from Dow Chemical), a phosphoric ester of three lauryl alcohol ether with 3 EO (such as Trilaureth-4 Phosphate from Clariant) and mixtures thereof,
- polyoxyethylene $C_{16-60}$ hydroxylesters containing 10 to 40 EO units, such as polyoxyethylenesorbitan monooleate (for examples sorbitol monoesters with oleic, myristic, stearic or palmitic acid, e.g. sorbitol monoester with a fatty acid which are polyethoxylated and containing 10 to 40 EO units also known as those known under the tradenames Tweens® by ACROS Organics (Geel, Belgium)), or such as polyethoxylated castor oils triglyceride containing 10 to 40 EO units such as e.g. Cremophor® RH 40 by BASF,
- $C_8$-$C_{20}$ mono- and polyglyceryl esters (such as Dermofeel® series commercialized by Dr. Streatmans Chemische Produkte GmbH Germany).

According to any one of the invention's embodiments, said non-ionic surfactant is an alkyl polyglucoside having an average polymerization degree of 1.1 to 2 and an average alkyl length of $C_{8-18}$. This type of surfactant is the most important sugar based surfactants and is particularly appreciated in the present context for their excellent performance, mildness, low interfacial tension and high dispersing power. Non-limiting examples of such alkyl polyglucosides are: Plantacare® 810UP, 818UP, 1200UP, 2000UP, (Plantacare® are derived from starch and fatty alcohols from palm kernel or coconut oil and are used in many cosmetic applications); and Lamesoft® PO 65, a composite based on alkyl polyglucoside and mono glyceryl oleate.

According to a particular embodiment of the invention, these non-ionic surfactants are used in a total amount of between about 1 and 15% by weight, and more preferably between about 4 and 10% by weight.

A second type of raw material of the solubilizing system, and optional, is a ionic surfactant.

When present, many different types of ionic surfactants can be used. In particular and as non-limiting examples one may cite those bellowing to the classes of:

- Anionic surfactants that include alkyl sulfosuccinate, sodium dioctyl sulfosuccinate (Aerosol® OT), sodium dihexyl sulfosuccinate (AMA), ammonium or sodium lauryl ether sulfate; $C_{8-22}$ salts of N-acyl amino acids such as taurate, sarcosinate, proline or glutamate (such as cocoyl proline sold as Natisol® by Sinerga); $C_{6-15}$ alkyl ether sulfates; $C_{7-24}$ alkyl ether sulfonates, or $C_6$-$C_{24}$ alkyl ether carboxylates (e.g. counterion can be sodium, ammonium, or potassium); alkyl sulfosuccinate can include a mono or dialkyl sulfosuccinate or a $C_{6-22}$ sulfosuccinate.
- Cationic surfactants that include a $C_{10-35}$ quaternary ammonium compound (e.g., an alkyldimethylammonium haloginide), $C_{20-30}$ alkyl pyridinium chlorides or bromides, or other hydrogenides or polyquaterny polymers such as e.g. hydroxyl ethyl cetyldimonium phosphate sold as Luviquat® Mono CP by BASF.

Amphoteric surfactants include, for example, a quaternary amino acid, an $C_{8-16}$ alkyl amine oxide, or a $C_{10-25}$ alkyl betaine.

According to any one of the invention's embodiments, these ionic surfactants are used in an amount of between about 0 and 12% by weight, and more preferably between about 0 and 5% by weight. According to a particular embodiments, these ionic surfactants are not used (i.e. 0%), i.e. the composition of the invention is free from ionic surfactant. According to another embodiment, the compositions of the invention are free from cationic surfactant. To the best of our knowledge, EtOH-free, transparent, stable microemulsion of perfumes devoid of ionic surfactant are also not known.

A fourth type of raw material of the invention's microemulsion, and mandatory, is a cooling hydrotrope. Said cooling hydrotrope is typically a cooling agent, as defined here-in above and which also acts as a hydrotrope. In fact it was surprisingly discovered that known cooling agents can also be used as hydrotrope in microemulsions.

Without the addition of said cooling hydrotrope the formation of microemulsion is not possible or requires higher surfactant concentration.

For the sake of clarity, by "hydrotrope" in the present invention it is meant a compound that is able to decrease the surfactant concentration necessary for microemulsion formation at given oil concentration, increase the solubilisation capacity of the microemulsion. These molecules are surface active, i.e. decrease the surface tension of water but cannot replace totally the surfactant.

Cooling agents are known compounds and are disclosed in an abundant literature. According to a particular embodiment of the invention, the cooling agents having $C_{10-25}$ and comprising one or two 2-isopropyl-5-methylcyclohexan-1-yl or 5-methyl-2-(prop-1-en-2-yl)cyclohexan-1-yl moieties, or a 2-isopropyl-5-methylcyclohexan-1,1-diyl or a 5-methyl-2-(prop-1-en-2-yl)cyclohexan-1,1-diyl moiety, or a $C_{4-10}$ α-branched alkyl group are particularly appreciated.

According to any one of the invention's embodiments, the cooling agents having $C_{10-16}$ and comprising a 2-isopropyl-5-methylcyclohexan-1-yl, 2-isopropyl-5-methylcyclohexan-1,1-diyl, 5-methyl-2-(prop-1-en-2-yl)cyclohexan-1-yl or 5-methyl-2-(prop-1-en-2-yl)cyclohexan-1,1-diyl moiety and one to three OH group are particularly appreciated. Alternatively, the cooling agents having $C_{7-11}$ and comprising a $C_{6-10}$ α-branched alkyl group and/or one CONHMe group are particularly appreciated.

According to any one of the invention's embodiments, said cooling agent is a natural extract containing at least 50% by weight of (−)-cubebol, or (−)-(1R,4S,5R,6R,7S,10R)-7-isopropyl-4,10-dimethyl-tricyclo[4.4.0.0(1,5)] decan-4-ol, e.g. as described in EP 104076.

Typically, and as non limiting examples, one may cite specifically the following cooling agents: (−)-menthol, (−)-cubebol, L-menthyl lactate, menthone 1,2-glycerol ketal (also known as menthone glycerin acetal or as 9-methyl-6-(1-methylethyl)-1,4-dioxaspiro-[4,5]decan-2-methanol), 2-isopropyl-N,2,3-trimethylbutanamide (also known as WS-23), N-(2-hydroxyethyl)-2,3-dimethyl-2-isopropylbutyramide (also known as WS-3), isopulegol (also known as Coolact™ P), menthyl ethoxyhydroxyacetate (also known as (1R,3R,4S)-3-p-menthanyl (2-hydroxyethoxy)acetate, see EP 1034161), menthoxypropanediol (also known as Cooling agent 10, or as 3-(menthoxy)-1,2-diol-propane); menthyl succinate (also known as (1R)-(−)-dimenthyl succinate or as bis(2-isopropyl-5-methylcyclohexyl) succinate), menthol ethylene glycol carbonate (also known as 2-hydroxyethyl ((2S,5R)-2-isopropyl-5-methylcyclohexyl) carbonate or Frescolat® MGC), menthol propylene glycol carbonate (also known as 2-hydroxypropyl ((2S,5R)-2-isopropyl-5-methylcyclohexyl) carbonate or Frescolat® MPC), 3-hydroxymethyl p-menthane, or mixtures thereof.

According to any one of the invention's embodiments, said hydrotrope is a mixture of WS3:WS23:propylene glycol (e.g. a w/w mixture of 25:25:50), WS23, menthyl lactate, menthone 1,2-glycerol ketal and/or menthoxypropanediol.

According to any one of the invention's embodiments, said hydrotrope is present in an amount of about 0.01 to 12%, preferably in an amount of 0.01% to 4% and more preferably in an amount of about 0.5% to 2.5% by weight.

The invention further relates to the use of a cooling agent, as defined above, to act as a hydrotrope to replace a portion of surfactant to form a transparent, clear microemulsion that is free of volatile organic solvents. The preferred microemulsion comprises the ingredients and concentrations disclosed herein.

According to a particular embodiment of the invention, the invention microemulsion may optionally further comprise one or more additional ingredients providing some specific added benefits, such as preservatives or additives, emollients and/or chelating agents.

Such additional ingredients are known compounds to a person skilled in the art and do not warrant a detail description. Moreover such additional ingredients can be synthetic or being natural.

According to a particular embodiment of the invention, said additional ingredients are present in an amount comprised between 0.0% and 5.0% w/w.

Another aspect of the present invention is a perfumed consumer product comprising the invention's perfuming compositions. The consumer product is typically a cologne, lotion, body splash or body mist.

The so-called "Body splash" is defined as body care formulation that is applied to the body after bathing and provides a subtle hint of scent. For people who cannot tolerate strong perfumes, these body splash formulations are an appealing alternative and represent a particular embodiment of the invention.

A body splash comprising an ethanol-free perfuming composition according to the invention which comprise about 3-8% of fragrance oil and having alkyl polyglucosides as non-ionic surfactants is a particular aspect of the present invention.

EXAMPLES

The following examples illustrate the most preferred embodiments of the invention without being limitative in nature.

A model perfume oil (fragrance D) with a log Pmix of about 2.12 was prepared by admixing the following ingredients:

| Perfume ingredients | Parts by weight |
|---|---|
| Di-Propyleneglycol | 55.04 |
| Star anise oil | 14.30 |
| Dihydromyrcenol | 8.60 |
| *Eucalyptus* oil | 4.60 |
| Hexylcinnamic aldehyde | 3.30 |
| Tricyclo[5.2.1.0(2,6)]dec-3-en-8-yl acetate | 3.30 |
| Coranol[1] | 2.30 |
| Isobornyl acetate | 1.60 |
| Dihydroestragole | 1.40 |

TABLE 1

Composition 1

| Ingredient | Function | % by wt |
|---|---|---|
| Water | | 73 |
| 1,3 Propanediol[1] | Solvent | 6.83 |
| Lamesoft ® PO 65 (Coco Glucoside; Glyceryl Oleate)[2]** | Non-ionic surfactant | 1.54 |
| $C_{11-15}$ Pareth-9/PPG-24 Buteth 26** | Non-ionic surfactant | 2.27 |
| Cooling agent mixture[3] | Cooling hydrotrope | 2.52 |
| Additives | | 1.34 |
| Fragrance D | Oil | 11.02 |
| Plantacare ® 2000 UP (Decyl Glucoside)[2]** | Non-ionic surfactant | 1.48 |
| Total Surfactant | | 7.56 |
| Remarks | Clear and transparent | Stable |

[1] Zemea ® marketed by DuPont Tate & Lyle
[2] Marketed by BASF
[3] A w/w mixture of 25:25:50 of (WS3 (N-ethyl-p-menthane-3-carboxamide):WS23 (2-iso-propyl-N,2,3-trimethylbutyramide):1,3-Propanediol)

TABLE 2

Composition 2

| Ingredient | Function | % by wt |
|---|---|---|
| Water | | 69.02 |
| 1,3 Propanediol | Solvent | 4.96 |
| Habo Monoester P90 ®[1] (Sucrose Palmitate) | Non-ionic surfactant | 1.13 |
| Lamesoft ® PO 65** | Non-ionic surfactant | 4.36 |
| Plantacare ® 818 UP (Coco Glucoside)[2]** | Non-ionic Surfactant | 2.08 |
| Plantacare ® 810 UP (Caprylyl/Capryl Glucoside)[2]** | Non-ionic Surfactant | 0.77 |
| Cetiol ® C5 (Coco-Caprylate)[3] | Emollient | 2.17 |
| Cetiol ® CC (Dicaprylyl Carbonate)[3] | Emollient | 1.65 |
| Cooling mixture[4] | Cooling hydrotrope | 2.50 |
| Additives | | 0.83 |
| Fragrance D | Oil | 10 |
| Plantacare ® 2000 UP** | Non-ionic surfactant | 0.53 |
| Total Surfactant | | 8.87 |
| Remarks | Clear and transparent | Stable |

[1] Marketed by Compass Foods
[2] Marketed by BASF
[3] marketed by Cognis
[4] A w/w mixture of 25:25:50 of (WS3:WS23:1,3-Propanediol)

TABLE 3

Composition 3

| Ingredient | Function | % by wt |
|---|---|---|
| Water | | 77.16 |
| 1,3 Propanediol | Solvent | 6.06 |
| Lamesoft ® PO 65** | Non-ionic surfactant | 2.86 |
| Plantacare ® 818 UP** | Non-ionic surfactant | 0.91 |
| Cetiol ® C5 (Coco-Caprylate) | Emollient | 2.47 |
| Cooling mixture[1] | Cooling hydrotrope | 2.00 |
| Additives | | 1.00 |
| Fragrance D | Oil | 5.01 |
| Plantacare ® 2000 UP** | Non-ionic surfactant | 2.53 |
| Total Surfactant | | 6.3 |
| Remarks | Clear and transparent | Stable |

[1] A w/w mixture of 25:25:50 of (WS3:WS23:1,3-Propanediol)

TABLE 4

Composition 4

| Ingredient | Function | % by wt |
|---|---|---|
| Water | | 87.73 |
| Plantacare ® 818 UP** | Non-ionic surfactant | 1.37 |
| Plantacare ® 810 UP** | Non-ionic surfactant | 2.1 |
| Natisol ® (Cocoyl Proline)[1]** | Anionic surfactant | 2.07 |
| Chlorhexidin Gluconate[2] | Preservative | 0.64 |

| Perfume ingredients | Parts by weight |
|---|---|
| 2,4-Dimethyl-3-cyclohexene-1-carbaldehyde | 1.45 |
| Linalol | 1.10 |
| Habanolide ®[2] | 0.85 |
| 1,4-Dioxacycloheptadecane-5,17-dione | 0.60 |
| Benzyl salicylate | 0.50 |
| 2-Methylundecanal | 0.30 |
| 2-Ethyl-4-(2,2,3-trimethyl-3-cyclopenten-1-yl)-2-buten-1-ol | 0.20 |
| 3-(1,3-Benzodioxol-5-yl)-2-methylpropanal | 0.15 |
| Helvetolide ®[3] | 0.15 |
| Terpineol | 0.15 |
| Cashmeran ®[4] | 0.10 |
| (Z)-3-Hexen-1-yl acetate | 0.07 |
| 2-Undecanone | 0.06 |
| Cis 2-Pentylcyclopentan-1-ol | 0.04 |
| Dodecanal | 0.03 |
| Rose oxide | 0.01 |
| Total | 45.16 |

[1] 4-cyclohexyl-2-methyl-2-butanol; origin: Firmenich SA, Geneva, Switzerland
[2] pentadecenolide; origin: Firmenich SA, Geneva, Switzerland
[3] (1S,1'R)-2-[1-(3',3'-dimethyl-1'-cyclohexyl)ethoxy]-2-methylpropyl propanoate; origin: Firmenich SA, Geneva, Switzerland
[4] 1,2,3,5,6,7-hexahydro-1,1,2,3,3-pentamethyl-4-indenone; origin: International Flavors & Fragrances, USA

Example 1

Various compositions according to the invention where obtained by admixing the ingredients as shown in the Tables herein below:

TABLE 4-continued

Composition 4

| Ingredient | Function | % by wt |
|---|---|---|
| WS 23 (2-isopropyl-N,2,3-trimethylbutyramide) | Cooling Hydrotrope | 0.86 |
| Cooling 10 (3-(1-Menthoxy)propane-1,2-diol) | Cooling Hydrotrope | 0.21 |
| Fragrance D | Oil | 5.02 |
| Total Surfactant | | 5.54 |
| Remarks | Clear and transparent | Stable |

[1] Marketed by Sinerga
[2] Marketed by ICI

TABLE 5

Composition 5

| Ingredient | Function | % by wt |
|---|---|---|
| Water | | 74.28 |
| Plantacare ® 818 UP** | Non-ionic surfactant | 1.32 |
| Plantacare ® 810 UP** | Non-ionic surfactant | 2.11 |
| Natisol ®** | Anionic surfactant | 1.64 |
| Chlorhexidin Gluconate | Preservative | 0.62 |
| Propylene Glycol[1] | Solvent | 14.03 |
| WS 23 | Cooling Hydrotrope | 0.87 |
| Cooling 10 | Cooling Hydrotrope | 0.16 |
| Fragrance D | Oil | 4.97 |
| Total Surfactant | | 5.07 |
| Remarks | Clear and transparent | Stable |

[1] Marketed by Carlo Erba

TABLE 6

Composition 6

| Ingredient | Function | % by wt |
|---|---|---|
| Water | | 70.75 |
| Symbio ®solve XC[1]** | Anionic surfactant | 2.91 |
| Plantacare ® 2000 UP** | Non-ionic surfactant | 1.24 |
| Propylene Glycol | Solvent | 19.54 |
| Cooling 10 | Cooling Hydrotrope | 0.32 |
| Fragrance D | Oil | 5.24 |
| Total Surfactant | | 4.13 |
| Remarks | Clear and transparent | Stable |

[1] Symbio ®solve XC sold by Dr. Straetmans Germany: Caprylyl/Capryl Wheat Bran/Straw Glycosides; Aqua; Fusel Wheat Bran/Straw Glycosides; Polyglyceryl-5 Oleate; Sodium Cocoyl Glutamate; Glyceryl Caprylate

TABLE 7

Composition 7

| Ingredient | Function | % by wt |
|---|---|---|
| Water | | 10.68 |
| Propylene Glycol | Solvent | 10.45 |
| Habo Monoester P90 | Non-ionic surfactant | 3.97 |
| Lamesoft ® PO 65** | Non-ionic surfactant | 10.07 |
| Plantacare ® 818 UP** | Non-ionic surfactant | 3.88 |
| Plantacare ® 810 UP** | Non-ionic surfactant | 1.73 |
| Plantacare ® 2000 UP** | Non-ionic surfactant | 1.01 |
| Cetiol Sensoft (Propylheptyl)[1] | Emollient | 13.27 |
| Cooling 10 | Cooling Hydrotrope | 5.28 |
| Fragrance D | Oil | 39.67 |
| Total Surfactant | | 20.66 |
| Remarks | Clear and transparent | Stable |

[1] Marketed by Cognis
**Active matter in surfactants:

| Surfactant | % active |
|---|---|
| Lamesoft ® PO 65 | 65-68 |
| Plantacare ® 818 UP | 51-53 |
| Plantacare ® 810 UP | 62-65 |
| Plantacare ® 2000 UP | 51-55 |
| Plantacare ® 1200 UP | 50-53 |
| Symbio ®solve XC | 70 |
| Natisol ® | 60 |
| $C_{11-15}$ Pareth-9/PPG-24 Buteth 26 | 50 |

Comparative Examples 1 to 3

Various microemulsion compositions where obtained by admixing the ingredients as shown in the Tables herein below:

TABLE 8

Comparative example 1 (According to U.S. Pat. No. 5,468,725)

| Ingredient | Function | % by wt "invention" | % by wt "Out of invention" |
|---|---|---|---|
| Water | | 95.33 | 95.91 |
| Cremophor ® RH 40 (Polyoxyl castor oil)[1] | Non-ionic surfactant | 1.99 | 2.01 |
| Luviquat ® Mono CP (Hydroxyethyl cetyldimonium phosphate)[1] | Cationic Surfactant | 0.08 | 0.08 |
| Cooling 10 | Cooling Hydrotrope | 0.61 | 0.00 |
| Fragrance D | Oil | 2 | 2 |
| Total Surfactant | | 2.07 | 2.09 |
| Remarks | | Clear and transparent | Opalescent |

[1] Marketed by BASF

Total surfactant concentration necessary to obtain a clear microemulsion with formulation "out of the invention" was: 5.2% (i.e. the cooling agent allow to use less than 50% of the surfactant usually necessary)

TABLE 9

Comparative example 2 (according to US 2011/0177995)

| Ingredient | Function | % by wt in active "invention" | % by wt "Out of invention" |
|---|---|---|---|
| Water | | 74.29 | 75.30 |
| Cremophor ® RH 40 | Non-ionic surfactant | 1.50 | 1.52 |
| Aerosol ® OT (Dioctyl sulfosuccinate sodium salt)[1] | Cationic surfactant | 1.50 | 1.52 |
| Plantacare ® 1200 UP (Lauryl Glucoside)[2] | Non-ionic surfactant | 1.50 | 1.50 |
| Hexylene Glycol | Solvent | 10.00 | 10.13 |
| Cooling 10 | Cooling Hydrotrope | 1.21 | 0.00 |

TABLE 9-continued

Comparative example 2 (according to US 2011/0177995)

| Ingredient | Function | % by wt in active "invention" | % by wt "Out of invention" |
|---|---|---|---|
| Fragrance D | Oil | 10 | 10.01 |
| Total Surfactant | | 4.50 | 4.54 |
| Remarks | | Clear and transparent | Opalescent |

1) Marketed by Aldrich
2) Marketed by Cognis

Total surfactant concentration necessary to obtain a clear microemulsion with formulation "out of the invention" was: 7.5% (i.e. the cooling agent allow to use less than 40% of the surfactant usually necessary)

TABLE 10

Comparative example 3 (according to US 2011/0177995)

| Ingredient | Function | % by wt in active "invention" | % by wt "Out of invention" |
|---|---|---|---|
| Water | | 79.13 | 79.32 |
| Cremophor ® RH 40 | Non-ionic surfactant | 1.49 | 1.49 |
| Aerosol ® OT | Cationic surfactant | 1.48 | 1.48 |
| Hexylene Glycol | Solvent | 10.10 | 10.11 |
| 1,3 Butylene Glycol | Solvent | 2.56 | 2.58 |
| Menthoxypropanediol | Cooling Hydrotrope | 0.24 | 0.00 |
| Fragrance D | Oil | 5 | 5.02 |
| Total Surfactant | | 2.97 | 2.97 |
| Remarks | | Clear and transparent | Opalescent |

Total surfactant concentration necessary to obtain a clear microemulsion with formulation "out of the invention" could not be determined because it was found impossible to obtain a clear microemulsion with such fragrance without using the cooling agent.

What is claimed is:

1. A transparent and ethanol-free microemulsion for replacement of ethanol containing microemulsions in perfuming applications comprising:
   0.5% to 50% of a fragrance-oil;
   1% to 36% of a solvent;
   a surfactant system comprising:
   a) at least one non-ionic surfactant present in an amount of 1% to 35%; and
   b) at least one ionic surfactant present in an amount of 0% to 12%;
   0.01% to 12% of at least one cooling hydrotrope that is not a surfactant and that evokes or prolongs a sensation of cold by modulation of the transient receptor potential (TRP) ion channels present in cold-sensitive nerve fibers of a user's skin or tongue, that has solubilizing properties, and is present in an amount which reduces the amount of surfactant needed to solubilize the oil in the microemulsion; and
   water;
   wherein the perfuming composition remains stable during freeze-thaw cycles from −25° C. to 50° C., and wherein all concentrations are based on the weight of the composition; and
   wherein the cooling hydrotrope is (−)-menthol, (−)-cubebol, L-menthyl lactate, menthone 1,2-glycerol ketal, N-(2-hydroxyethyl)-2,3-dimethyl-2-isopropylbutyramide (WS3), 2-isopropyl-N,2,3-trimethylbutanamide (WS23), a mixture of WS3 and WS23, isopulegol, menthyl ethoxyhydroxyacetate, menthoxypropanediol; menthyl succinate, menthol ethylene glycol carbonate, menthol propylene glycol carbonate, 3-hydroxymethyl p-menthane or mixtures thereof.

2. The microemulsion according to claim 1, wherein the fragrance oil is present in an amount of 0.5% to 15% of the microemulsion.

3. The microemulsion according to claim 1, wherein the solvent is selected from the group consisting of propylene glycol, dipropyleneglycol, diethyl phthalate, isopropyl myristate, benzyl benzoate, 2-(2-ethoxyethoxy)-1-ethanol, ethyl citrate and 1,2-alkanediols with 5-10 carbons.

4. The microemulsion according to claim 1, wherein the non-ionic surfactant is selected from the group consisting of:
   sugar ester compound;
   $C_{8-22}$-alkyl polyglucoside;
   ethoxylated aliphatic $C_6$-$C_{20}$ alcohol containing 2 to 30 EO and/or PO units;
   polyoxyethylene $C_{16-60}$ hydroxylester containing 10 to 40 EO units; and
   $C_8$-$C_{20}$ mono- and polyglyceryl ester.

5. The microemulsion according to claim 1, wherein the non-ionic surfactant is used in a total amount of between 1 and 15% by weight.

6. The microemulsion according to claim 1, wherein the ionic surfactant is selected from the group consisting of alkyl sulfosuccinates, sodium dioctyl sulfosuccinate, sodium dihexyl sulfosuccinate, ammonium or sodium lauryl ether sulfate, $C_{8-22}$ salts of N-acyl amino acid, $C_{6-15}$ alkyl ether sulfates, $C_{7-24}$ alkyl ether sulfonates, $C_6$-$C_{24}$ alkyl ether carboxylates, $C_{10-35}$ quaternary ammonium compounds, $C_{20-30}$ alkyl pyridinium chlorides or bromides, hydroxyl ethyl cetyldimonium phosphate; quaternary amino acid, $C_{8-16}$ alkyl amine oxides and $C_{10-25}$ alkyl betaines.

7. The microemulsion according to claim 1, wherein the ionic surfactant is used in a total amount of no more than 5% by weight.

8. The microemulsion according to claim 1, wherein the solvent/surfactant system w/w ratio is 0.2 to 4.

9. The microemulsion according to claim 1, wherein the cooling hydrotrope is present in an amount of 0.01 to 4% by weight.

10. The microemulsion according to claim 1, which is free from ionic surfactant.

11. A perfumed consumer product comprising a perfuming composition according to claim 1.

12. The perfumed consumer product according to claim 11, in the form of a cologne, lotion, body splash or body mist.

13. The perfumed consumer product according to claim 11, in the form of a body splash wherein the fragrance oil is present in an amount of 3% to 8% and the non-ionic surfactants include one or more alkyl polyglucosides.

14. A transparent, clear microemulsion that is free of volatile organic solvents comprising:
   1% to 36% of propylene glycol, dipropyleneglycol, diethyl phthalate, isopropyl myristate, benzyl benzoate, 2-(2-ethoxyethoxy)-1-ethanol, ethyl citrate or an 1,2-alkanediol having 5-10 carbons;
   a surfactant system comprising:
   a) at least a non-ionic surfactant present in an amount of 1% to 35%; and
   b) at least an ionic surfactant present in an amount of 0% to 12%;
   0.01% to 12% of at least a cooling hydrotrope that is not a surfactant and that evokes or prolongs a sensation of cold by modulation of the transient receptor potential (TRP) ion channels present in cold-sensitive nerve fibers of a user's skin or tongue, that has solubilizing properties, and is present in an amount which reduces the amount of surfactant needed to solubilize the oil in the microemulsion; and water;

wherein the microemulsion remains stable during freeze-thaw cycles from −25° C. to 50° C., and wherein all concentrations are based on the weight of the composition; and wherein the cooling hydrotrope is (−)-menthol, (−)-cubebol, L-menthyl lactate, menthone 1,2-glycerol ketal, N-(2-hydroxyethyl)-2,3-dimethyl-2-isopropylbutyramide (WS3), 2-isopropyl-N,2,3-trimethylbutanamide (WS23), a mixture of WS3 and WS23, isopulegol, menthyl ethoxyhydroxyacetate, menthoxypropanediol; menthyl succinate, menthol ethylene glycol carbonate, menthol propylene glycol carbonate, 3-hydroxymethyl p-menthane or mixtures thereof.

15. A perfuming composition comprising the microemulsion of claim 14 and 0.5% to 50% of a fragrance oil.

16. A perfumed consumer product comprising a perfuming composition according to claim 15 in the form of a body splash wherein the fragrance oil is present in an amount of 3% to 8% and the non-ionic surfactants include one or more alkyl polyglucosides.

17. The microemulsion according to claim 14, which is free from ionic surfactant.

18. The microemulsion according to claim 14, which is free from cationic surfactant.

19. The microemulsion according to claim 1, which is free from cationic surfactant.

* * * * *